(12) United States Patent
Sauvan et al.

(10) Patent No.: US 7,527,813 B2
(45) Date of Patent: May 5, 2009

(54) **COSMETIC COMPOSITION CONTAINING AN EXTRACT OF *LIMNOCITRUS LITTORALIS***

(75) Inventors: Nancy Sauvan, Orleans (FR); Isabelle Renimel, Trainou (FR); Cécile Lamy, Saint Jean de Braye (FR); Delphine Dupont, Dourdan (FR)

(73) Assignee: LVMH Recherche, Saint Jean de Braye ( * ) Notice: Subject to any disclaimer, the term of this patent is extended or adjusted under 35 U.S.C. 154(b) by 0 days.

(21) Appl. No.: 11/805,390

(22) Filed: May 23, 2007

(65) Prior Publication Data

US 2008/0031981 A1   Feb. 7, 2008

(30) Foreign Application Priority Data

Jul. 4, 2006   (FR)   ................... 06 52784

(51) Int. Cl.
*A61K 36/00*   (2006.01)
(52) U.S. Cl. ..................................... 424/725
(58) Field of Classification Search ............... None
See application file for complete search history.

(56) References Cited

FOREIGN PATENT DOCUMENTS

| FR | 2837702 | 10/2003 |
|---|---|---|
| JP | 05-310551 A | 11/1993 |
| JP | 06-080576 A | 3/1994 |
| JP | 11-209224 A | 8/1999 |
| KR | 10-2001-0018805 A | 3/2001 |
| KR | 10-2006-0014714 A | 2/2006 |

OTHER PUBLICATIONS

Herbal Preparations. Jan. 7, 2006. Retrieved from the internet: <http://web.archive.org/web/20060107183147/http://www.herbsandnaturalremedies.com/herbalpreparations.htm>. Retrieved on Jun. 19, 2008.*
Herb Health Guide. Aug. 22, 2005. Retrieved from the internet: <http://web.archive.org/web/20050802235209/http://www.herb-health-guide.com/how-to-prepare-herbal-remedies.html>. Retrieved on Jun. 19, 2008.*
Darnault et al. "Techniques séparatives: Approche phytochimique par HPTLC: Support à la selection de plantes actives en cosmétologie" Apr. 13, 2006. XP002427844 <http://www.forumlabo.com/2006/abstracts/2006/theme5/phyto.htm>.
Anonymous: "Techniques séparatives" Forum Labo & Forum Biotech. Apr. 2, 2007. XP002427845 <http://www.forumlabo.com/cgi-bin/glob-search-frames2.cgi?K=lvmh&Z=1&result_par_page=10&case=Insensitive>.
Combined Search and Examination Report Issued by UK Intellectual Property Office Aug. 30, 2007.
Table of Contents from The Citrus Industry, vol. I: History, World Distribution, Botany, and Varieties http://lib.ucr.edu/agnic/webber/Vol1/Vol1TOC.html.

* cited by examiner

*Primary Examiner*—Christopher R. Tate
*Assistant Examiner*—Melenie McCormick
(74) *Attorney, Agent, or Firm*—Hamre, Schumann, Mueller & Larson, P.C.

(57) ABSTRACT

The invention relates to a cosmetic composition, characterized in that it contains, as active agent, an extract of *Limnocitrus littoralis* obtained by extraction with an extraction solvent selected from the group comprising alcohols and aqueous-alcoholic mixtures, in a cosmetically acceptable vehicle compatible with topical application.

It further relates to a method of cosmetic treatment intended especially for soothing non-pathological skin manifestations of inflammatory origin and/or preventing and/or combating the effects of intrinsic and/or photoinduced ageing, comprising the application to the skin of a cosmetic composition of the invention.

23 Claims, No Drawings

COSMETIC COMPOSITION CONTAINING AN EXTRACT OF *LIMNOCITRUS LITTORALIS*

The present invention relates to the field of cosmetics. It relates more particularly to novel cosmetic compositions comprising an extract of *Limnocitrus littoralis* (Miq.) Swingle, hereafter denoted as *Limnocitrus littoralis*, and to novel uses of this extract in the field of cosmetics.

*Limnocitrus littoralis* is a plant of the Rutaceae family with the basionym *Paramignya littoralis* Miq. It originates from south-east Asia and, according to our information, is the only species so far indexed in the genus *Limnocitrus*. Its habitat is essentially located in hot and dry zones.

They are shrubs in the form of bushes that are found essentially, but not uniquely, in Vietnam, which is moreover the origin of those used in the description of the present invention.

Traditional or religious uses of this plant are related in legends and in Vietnamese literature. There have also been descriptions of uses and traditional therapeutic effects, especially of the leaves of *Limnocitrus littoralis*, as an expectorant, antitussive product or for preparing steam baths considered to be effective remedies for exudation and the treatment of colds and fevers.

Different uses in traditional medicine, either of the roots as an antipyretic, or of the leaves as an antitussive, or of the pericarp for treating asthma attacks or cough, are also known.

Finally, various traditional remedies, especially for metritis, constipation and cough, propose decoctions containing, inter alia, either fresh or dried parts of *Limnocitrus littoralis*.

The use of burnt leaves for their fragrant smoke has also been described.

The Rutaceae family, to which *Limnocitrus littoralis* belongs, comprises especially the genus *Citrus*, which is very widespread and very well known and includes about 165 species.

It is known that a number of plant species belonging to the genus *Citrus* have anti-inflammatory properties. However, this anti-inflammatory character is far from general.

The inventors were therefore also interested in plants species belonging to the genus *Citrus* even if their botanical genus was different from that of *Limnocitrus littoralis*.

Thus, conversely, certain plant species of the genus *Citrus* have a pro-inflammatory character. Furthermore, as demonstrated by the experiments carried out by the Applicant, other plant species of the genus *Citrus* are toxic on the model used at doses for which they have an anti-inflammatory activity.

The inventors of the present invention have now discovered, by testing different plant species of the genus *Citrus*, that it is possible to prepare, from the plant *Limnocitrus littoralis*, extracts that are non-toxic at the doses used and at the same time particularly active in cosmetics.

More precisely, in the course of systematic experiments, the inventors of the present invention have been able to select extracts that are remarkably suitable for combating non-pathological skin manifestations of inflammatory origin, particularly those associated with sensitive skin, by means of a soothing effect.

Sensitive skin is understood as meaning skin which responds to external aggressions with the same signs as so-called normal skin, but more rapidly and sometimes more violently, without said skin exhibiting a pathological state.

Non-pathological manifestations generally associated with sensitive skin are well known. They result in more or less pronounced sensations of discomfort on the skin, depending on the person in question, and especially in sensations of heat or burning, tingling, itching and/or pulling, or else in the appearance of blotches. These skin disorders are caused by external factors such as emotions, environmental factors (pollution, UV, tobacco, temperature, etc.) and chemical agents present especially in cosmetic compositions, such as surfactants, preservatives, perfumes or certain cosmetic active agents.

The mechanisms of action that lead to these manifestations are variously understood, but inflammatory processes are both a common feature and the origin thereof. These processes lead to a greater or lesser excitation of the sensitive cutaneous nerves, following the release of inflammation mediators such as reactive oxygen species, cytokines (like interleukin-8) or prostaglandins, particularly type $E_2$ prostaglandins.

Furthermore, the inventors have been able to ascertain that these same extracts prove effective in other cosmetic applications, particularly in the field of skin ageing, on account of their ability to stimulate collagen synthesis.

Thus, according to a first feature, the invention relates to a cosmetic composition comprising an extract of the plant *Limnocitrus littoralis*.

According to a second feature, the invention relates to the use of said extract as an active agent in compositions in order to give them different cosmetic properties for combating non-pathological skin manifestations of inflammatory origin and preventing and/or combating the effects of skin ageing.

According to a third feature, the invention relates to a method of cosmetic treatment for skin care, particularly for the purpose of combating non-pathological skin manifestations of inflammatory origin or preventing and/or combating the effects of skin ageing, particularly anti-wrinkle care.

Thus, according to a first essential characteristic, the invention relates to a cosmetic composition, characterized in that it comprises, as active agent, an extract of *Limnocitrus littoralis* obtained by means of an alcoholic or aqueous-alcoholic extraction solvent, in a cosmetically acceptable vehicle compatible with topical application.

According to a second essential characteristic, the invention relates to the use, in a cosmetic composition or for the manufacture of a cosmetic composition, of an extract of *Limnocitrus littoralis* of the invention as active agent, giving said cosmetic composition cosmetic properties for combating non-pathological skin manifestations of inflammatory origin, such as those associated with sensitive skin, by means of a soothing effect.

According to this first use, the invention relates to the use of said cosmetic composition for soothing non-pathological skin manifestations of inflammatory origin, such as sensations of heat or burning, blotches, pulling, itching and tingling.

According to a second use, the invention relates to the use, in a cosmetic composition or for the manufacture of a cosmetic composition, of an extract of *Limnocitrus littoralis* according to the invention as an agent for stimulating collagen synthesis.

According to this second use, the invention relates to the use of said composition for preventing and/or combating the effects of intrinsic and/or photoinduced skin ageing.

According to another essential characteristic, the invention relates to a method of cosmetic care intended especially for soothing non-pathological skin manifestations of inflammatory origin and/or preventing and/or combating the effects of intrinsic and/or photoinduced ageing, comprising the application to the skin of a cosmetic composition according to the invention.

According to this last characteristic, the invention relates more particularly to a method of cosmetic care for anti-wrinkle care.

Other characteristics of the invention will become apparent from the following description and detailed Examples.

The cosmetic compositions of the invention are characterized by the presence of an active agent consisting of an extract of *Limnocitrus littoralis*.

This extract is obtained by a process comprising at least one extraction step with an alcoholic or aqueous-alcoholic extraction solvent.

The experiments carried out by the inventors of the present invention have shown that it is preferable to use the aerial parts of the plant in order to obtain the extracts useful according to the invention.

In one particularly advantageous variant of the invention, the extract is an extract of leaves.

The alcohols used, be they pure or in an aqueous-alcoholic mixtures, are advantageously $C_1$ to $C_5$ monoalcohols or $C_2$ to $C_5$ glycols.

Ethanol, butylene glycol and ethanol/water and butylene glycol/water mixtures may be mentioned as particularly preferred alcohols for preparing the extracts useful according to the invention.

It became apparent in the course of the experiments carried out by the inventors of the present invention that the quality of the extracts, and especially the stability of their intrinsic properties over time, was appreciably improved when the extraction solvent contained relatively small amounts of water or was even anhydrous.

Thus, in one advantageous variant, the extraction solvent is ethanol or an ethanol/water mixture comprising at most 50% of water, preferably at most 4% of water.

In another particularly advantageous variant of the invention, the extract is obtained by using pure butylene glycol as extraction solvent.

Thus the extracts of *Limnocitrus littoralis* of the invention are advantageously obtained by using an anhydrous solvent and very particularly butylene glycol.

Furthermore, in one particularly advantageous embodiment, even if the extract is not obtained directly by extraction with butylene glycol, it proves valuable to introduce it into the composition of the invention in the form of a butylene glycol solution and particularly in the form of a solution containing from 0.05 to 5% by weight and preferably from 0.1 to 1% by weight of dry extract, based on the weight of butylene glycol.

In yet further variants, before the extract is introduced into a composition, and while it is still in solution in the extraction solvent used according to the invention, it will be subjected to a solid-liquid separation step in order to remove the solid part.

The extract may also be subjected to various decolorization steps and particularly to a decolorization step over activated charcoal.

The concentration of extract in the compositions of the invention, expressed as the percentage by weight of dry extract, may vary within wide limits.

However, this concentration will advantageously be between $10^{-4}$ and 5% by weight and preferably between 0.01 and 2% by weight of dry extract, based on the total weight of the composition, the extract preferably being an extract of leaves of *Limnocitrus littoralis*.

The compositions of the invention may comprise at least one preservative selected from the preservatives conventionally used in the field of cosmetics.

The compositions of the invention may also comprise at least one antioxidant.

Alpha-tocopherol, ascorbic acid and their cosmetically acceptable derivatives, especially their esters, may be mentioned as particularly preferred antioxidants according to the invention.

The compositions of the invention can be formulated in a large variety of ways and can be presented in any form compatible with topical application to the skin.

In particular, they can be presented in the form of a cream, gel, lotion, stick, eye shadow or make-up foundation.

The preferred compositions of the invention will comprise particularly reduced amounts of water or will be in anhydrous form.

Examples of such compositions which may be mentioned are make-up foundations, eye shadows or sticks.

As explained earlier, the value of the compositions is essentially associated with the properties for soothing non-pathological skin manifestations of inflammatory origin, and also with an activity in combating or preventing the effects of intrinsic and/or photoinduced skin ageing, particularly wrinkles.

The inventors of the present invention have demonstrated that the soothing properties are associated essentially with an activity in inhibiting type $E_2$ prostaglandins ($PGE_2$), and the anti-ageing activity with an activity in stimulating collagen synthesis.

By virtue of their properties, the extracts as defined above may be used as a skin soothing agent in cosmetic compositions or for the manufacture of these compositions.

The resulting compositions may be used for soothing non-pathological skin manifestations of inflammatory origin, such as sensations of heat or burning, tingling, blotches, pulling or itching, which are caused by inflammatory-type phenomena of the skin.

By virtue of their second type of activity in collagen synthesis, the extracts of the invention may be used as agents for stimulating collagen synthesis in cosmetic compositions or for the manufacture of such compositions.

Such compositions may be used in all cases where it is sought to prevent and/or combat the effects of intrinsic and/or photoinduced skin ageing, particularly wrinkles.

Said inflammatory-type phenomena mentioned above are also recognized as having a role in the acceleration of skin ageing, as described by S. Pillai, C. Oresajo and J. Hayward in the following article: International Journal of Cosmetic Science, 2005, 27, pp 17-34.

Thus, through their dual activity, on the one hand against non-pathological skin manifestations of inflammatory origin and on the other hand in stimulating collagen synthesis, the extracts according to the invention are particularly suitable for the field of skin ageing.

As explained earlier, the invention further relates to a method of cosmetic care intended especially for soothing skin disorders of inflammatory origin and/or preventing and/or combating the effects of intrinsic and/or photoinduced ageing, characterized in that it comprises applying to the skin a cosmetic composition as defined above.

EXAMPLES

I. Preparation of Extracts Useful According to the Invention a. Preparation of an Extract by Aqueous-ethanolic Extraction 150 ml of an ethanol/water mixture in proportions of 90/10 volume/volume (v/v) are added to 10 g of ground leaves in a 250 ml round-bottomed flask. The mixture is refluxed for 30 minutes. After cooling, the extract is filtered on a Büchner funnel with 2 GF/F filters (Whatman), after which the filter cake is rinsed with 50 ml of an ethanol/water mixture (90/10, v/v). The filtrate is then evaporated to dryness on a rotary evaporator.

The resulting dry extract is used to prepare 3 solutions:
- a 1% weight/volume (w/v) solution in an ethanol/water mixture (50/50, v/v), hereafter called extract A,
- a 1% (w/v) solution in butylene-1,3-glycol, hereafter called extract B, and
- a 1% (w/v) solution in ethanol/water (50/50, v/v) with 30 µl/ml of a mixture containing antioxidants, hereafter called extract C.

This mixture of antioxidants is composed of 0.20 g of alpha-tocopherol+0.05 g of palmitoyl lecithin+0.01 g of ascorbyl palmitate, all in 6 ml of a water/ethanol mixture (16/84, v/v).

b. Preparation of an Extract by Extraction with Butylene Glycol 150 ml of butylene-1,3-glycol are added to 10 g of ground leaves in a 250 ml round-bottomed flask. The mixture is agitated for 1 hour at 50° C. After cooling, the extract is filtered on a Büchner funnel with one 0.45 µm filter (Millipore). The filter cake is rinsed with 50 ml of butylene-1,3-glycol. The dry extract of the solution is about 0.4% by weight, based on the total weight of the solution.

The resulting dry extract is hereafter called extract D.

c. Preparation of a Decolorized Extract

The butylene glycol solution obtained in b) is decolorized over activated charcoal (CxV) (supplied by CECA) following the procedure described below.

A first step is carried out on 50.07 ml of the above solution with 10 mg of activated charcoal (i.e. about 5% by weight, based on the weight of solids). The whole is agitated for 2 hours at room temperature. The solution is filtered on a GF/F filter (Whatman).

A further 10 mg of activated charcoal are added to this solution. The whole is agitated for 1 hour at room temperature. The solution is filtered on a GF/F filter (Whatman).

A further 20 mg of activated charcoal are added to this solution. The whole is agitated for 1 hour at room temperature. The solution is filtered on a GF/F filter (Whatman) and then evaporated to dryness.

The resulting dry extract of this solution is 0.28% by weight, based on the total weight of the solution. It is hereafter called extract E.

II. Demonstration of the Anti-Inflammatory Activity

1. Principle of the Test

The test is performed on human keratinocytes and its aim is to determine the inhibition of the release of type $E_2$ prostaglandin in the presence of extracts according to the invention.

2. Protocol of the Test for Measuring the Anti-inflammatory Activity a. Preparation of the Positive Reference and the Test Sample The positive reference used to inhibit the release of $PEG_2$ is indomethacin (Sigma ref.: I7378). A $3.10^{-3}$ molar stock solution was prepared in DMSO. Indomethacin was introduced into the culture medium at 0.1% v/v, i.e. at a final concentration of active ingredient of $3.10^{-6}$ M. An excipient reference (DMSO) at a final concentration of 0.1% v/v was prepared in parallel. Each extract of *Limnocitrus littoralis* to be tested is dissolved in DMSO at a concentration of 5% v/v and then diluted to a concentration of 3.125 mg/ml.

Each extract of *Limnocitrus littoralis* to be tested is then introduced into the culture medium at 0.1% v/v, i.e. at a final concentration of active ingredient of 3.125 µg/ml. An excipient reference (DMSO) at a final concentration of 0.1% v/v was prepared in parallel.

A cell viability test was carried out beforehand by the XTT method (after 24 hours of treatment) in order to verify the absence of cytotoxicity towards keratinocytes at the dose of *Limnocitrus littoralis* studied.

b. Treatment of the Cells

The keratinocytes (type HaCaT) are cultivated in a complemented KSFM (Gibco ref.: 17005-034+37000-015). The keratinocytes are inoculated into 96-well microplates at a rate of 10,000 cells per well. This first day of culture is considered as D0. After 24 hours of incubation (D1), the medium is replaced with KSFMc containing either an extract of *Limnocitrus littoralis* as described in item I, or indomethacin, or the solvent reference (DMSO).

After 48 hours (D3), i.e. 24 hours of treatment, the culture medium is recovered and then frozen at −20° C., and the cells are rinsed once with PBS and are subjected to a protein assay by the BCA method.

After thawing, the culture medium is assayed according to the protocol of the EIA (enzyme immunoassay) kit sold by Cayman under the reference 514010.

A calibration range according to the same protocol is established at the same time (range from 0 to 1 ng/ml).

c. Results

Table I below collates the results expressed as the percentage inhibition of type $E_2$ prostaglandins in the presence of extracts A, B, C, D and E, used at 1 mg/ml and 0.1 mg/ml in DMSO.

TABLE I

| Extract | 1 µg/ml | 0.1 µg/ml |
|---------|---------|-----------|
| A | 42% | 23% |
| B | 62% | 45% |
| C | 61% | 36% |
| D | 60% | 42% |
| E | 57% | 39% |

It is seen that extracts A, B, C, D and E all have a PEG-2 inhibitory activity and that, at a greater but not cytotoxic concentration, the PEG-2 inhibitory activity even becomes very significant.

III. Demonstration of the Value of *Limnocitrus littoralis* Compared with Other Plants Belonging to the Genus *Citrus*

The experiments described below illustrate the value of *Limnocitrus littoralis* compared with other *citrus* in terms of anti-inflammatory activity and toxicity.

In the study carried out in this part, the test described in part II above was used to determine the anti-inflammatory activity.

The study involved the following five species of the genus *Citrus*:

I: *Citrus maxima* (Burm. Ex Rumph.) Merr.
II: *Citrus aurentifolia* (Christm.) Swingle
III: *Citrus nobilis* (Lour.)
IV: *Citrus hystrix* (DC.)
V: *Citrus reticulata* (Blanco.)

The inventors of the present invention endeavored to compare the $PGE_2$ inhibitory capacities between extract A of *Limnocitrus littoralis* and aqueous-alcoholic extracts of various *citrus* obtained under the same extraction conditions as those described for extract A, and tested at identical concentrations.

Furthermore, the toxicity of extracts I to V was verified by comparison with that of extract A of *Limnocitrus littoralis* obtained under the same conditions.

1. Determination of the Cytotoxicity Limit

To determine the cytotoxicity limit, the acceptable non-cytotoxicity limit was taken to be the limit corresponding to a 90% cell viability.

The results are given in Table II below:

TABLE II

| Reference | Cytotoxicity limit |
|-----------|--------------------|
| *Limnocitrus littoralis* | 12.5 µg/ml |
| I | 12.5 µg/ml |
| II | 6.25 µg/ml |
| III | 3.125 µg/ml |
| IV | 80% viability at 0.19 µg/ml |
| V | 70% viability at 0.19 µg/ml |

Samples IV and V are considered cytotoxic under the experimental conditions used.

2. Determination of the Release of PEG$_2$

All the extracts were tested at 3.125 μg/ml under the conditions described in II b), the assay being effected using an EIA kit (ref.: 514010) marketed by Cayman. The extracts obtained from species IV and V of the genus Citrus exhibit a cytotoxicity plateau beyond this dose.

The values shown in the Table below are PEG$_2$ release percentages obtained by comparison between the PEG$_2$ release activity of a given sample and that of a reference without effector, whose PEG$_2$ release activity is arbitrarily fixed at 100% because it corresponds to the basal PEG$_2$ release activity of the cells.

TABLE III

|  | Limnocitrus littoralis | I | II | III | IV | V |
|---|---|---|---|---|---|---|
| PGE$_2$ release | −52 | −32.76 | 36.86 | 46.86 | 78.14 | 56.73 |
| Standard deviation | 12.59 | 14.96 | 15.86 | 20.22 | 36.90 | 9.16 |

This first result obtained over only 3 points (producing fairly high standard deviations) indicates that, with the model used and under the operating conditions, of all the species of the genus Citrus tested, only Citrus maxima (I) has a negative PGE$_2$ release of −32.76 relative to the reference, which in practice results in a PGE$_2$ inhibitory activity. It is also seen that this activity is substantially lower than that of Limnocitrus littoralis at −52, representing a much higher PGE$_2$ inhibitory capacity.

IV. Demonstration of the "Anti-Ageing" Activity

1. Principle and Object of the Test

Free radicals are involved in the acceleration of chronological skin ageing through their direct and indirect action via their pro-inflammatory activity. We therefore chose a model of oxidative stress by UVA and UVB radiation for simulating accelerated chronological ageing (Rittié et al., UV light-induced cascades and skin ageing. Ageing Research Review 2002, 2, 705-720).

The effects of extracts of Limnocitrus littoralis according to the invention on collagen synthesis was evaluated.

2. Experimental Model of Human Skin Kept Live and Subjected to an Oxidative Stress Skin fragments were obtained from women following plastic surgery (8 different donors). The fragments were placed in inserts, which were themselves suspended above culture wells. Culture medium is added to the bottom of the wells and passes between the two compartments by slow diffusion through a porous membrane (12 μm). This culture medium in the wells was renewed every 3 days.

An experimental model of oxidative stress was set up with a session (at D0) of irradiation with UVA (8 J/cm$^2$) and UVB (16 J/cm$^2$) so as to cause the generation of oxygenated free radicals. A test extract of Limnocitrus littoralis according to the invention is then applied to the surface of the skin once a day.

The protocol therefore comprises the following conditions:
reference skin (free of oxidative stress and untreated)
skin+oxidative stress (control skin)
skin+oxidative stress+test extract of Limnocitrus littoralis according to the invention The skin cultures were then stopped at D7 for the various analyses.

3. Analysis of the Effect of an Extract of Limnocitrus littoralis on Collagen Synthesis The effect of an extract of Limnocitrus littoralis on stimulation of the metabolism of the skin fibroblasts in terms of collagen synthesis is evaluated on the dermis by biochemical assay of the collagen.

The skin fragments are digested enzymatically overnight at +4° C. in 0.5 M acetic acid solution containing pepsin. This method makes it possible to recover the newly synthesized collagen. After mechanical grinding, e.g. with a Potter mill, the amount of collagen (μg/ml) is evaluated by a method of spectrocolorimetric assay at 540 nm: the acid-soluble collagen is detected after the specific fixation of Sirius red dye (Sircol Collagen Assay, Interchim).

The different results are compared by taking the ratio of the amount of collagen to the amount of total proteins in the sample. The protein concentration is assayed spectrophotometrically at 562 nm (BCA assay, Pierce).

The results are expressed in jig of collagen/mg of protein.

4. Statistical Analyses

A comparative study of the results was made between the skin fragments treated with an extract of Limnocitrus littoralis and the skin fragments which were untreated but had undergone an oxidative stress with UV; the study comprises:
reference skin
skin aged experimentally with UVA and UVB (control skin)
skin+UVA/UVB+extract of Limnocitrus littoralis according to the invention The results obtained over the 8 skin fragments were averaged.

The statistical analysis was performed by the so-called reduced deviation Student's t-test or paired sample t-test, with a 5% risk level.

5. Results of the Biochemical Collagen Assay

The results presented in Table IV were obtained with extract D.

TABLE IV

| Collagen synthesis (μg/mg of total proteins): | |
|---|---|
| | μg/mg |
| reference skin | 114.5 ± 32.2 |
| skin + UV | 87.3 ± 22.3 |
| | *p = 0.02 |
| skin + UV + extract D | 128.4 ± 52.6 |
| | #p = 0.04 |

*difference statistically significant relative to the reference skin (paired Student's t-test, p < 0.05)
difference statistically significant relative to the UV control skin (paired Student's t-test, p < 0.05)

It is seen on the one hand that there is a statistically significant decrease in collagen synthesis with a proportion of 87.3 μg/mg for the skin subjected to oxidative stress, compared with a proportion of 114.5 μg/mg for the reference skin (p=0.02).

It is seen on the other hand that treatment with extract D of Limnocitrus littoralis made it possible to obtain a statistically significant stimulation of collagen synthesis with a proportion of 128.4 μg/mg versus 87.3 for the control skin (p=0.04).

6. Conclusion

Using a model of human skin kept alive and subjected to an oxidative stress simulating accelerated skin ageing, we have demonstrated a statistically significant stimulation of collagen synthesis, thereby showing that an extract of Limnocitrus littoralis according to the invention has an anti-ageing activity.

V. Formulation Examples According to the Invention

The topical cosmetic compositions described below are prepared in conventional manner from the following centesimal compositions by weight.

| Gel | |
|---|---|
| Deionized water | 73.5% |
| Alcohol 96.2 vol % | 21 |
| AMPS polymer (Sepigel 305) | 3 |
| Preservative | 0.3 |
| Perfume concentrate | 0.1 |
| Extract D of *Limnocitrus littoralis* | 2 |
| Sodium hyaluronate (high molecular weight) | 0.1 |

| Body emulsion | |
|---|---|
| Octyl palmitate | 7.0% |
| Glyceryl caprylate/caprate triglycerides | 3.0 |
| Octyl octanoate | 2.0 |
| Phenyl trimethicone | 2.0 |
| Glycerol | 2.0 |
| Stearic acid | 1.0 |
| Sorbitan stearate | 1.0 |
| Cetyl alcohol | 0.5 |
| Stearyl alcohol | 0.5 |
| Extract E of *Limnocitrus littoralis* | 1 |
| Preservatives, perfume, colorants, neutralizer | 0.1 |
| Water | qsp |

| Lotion | |
|---|---|
| Butylene glycol | 3% |
| EDTA | 0.1 |
| Solubilizer | 1 |
| Perfume concentrate | 0.1 |
| Alcohol | 5.2 |
| Extract A of *Limnocitrus littoralis* | 0.5 |
| Benzophenone-4 | 0.13 |
| Preservatives, perfume, colorants, neutralizer | 0.1 |
| Water | qsp |

| Make-up foundation | |
|---|---|
| Polyglyceryl-4 isostearate/cetyl dimethicone copolyol/hexyl laurate (marketed e.g. under the name Abil WE 09) | 5.1% |
| Cyclopentasiloxane and cyclohexasiloxane (e.g. Fluid DC345 from Dow Corning) | 5.0 |
| Cetyl dimethicone (e.g. Abil wax 9840) | 1.0 |
| Caprylic/capric triglycerides | 2.2 |
| Octyl stearate | 1.4 |
| Mineral oil | 3.5 |
| Hydrogenated castor oil | 1.2 |
| Beeswax | 0.8 |
| Polymethyl methacrylate | 1.1 |
| Iron oxides | 0.5 |
| Titanium dioxide | 5.2 |
| Water | 67.3 |
| NaCl | 0.6 |
| Extract D of *Limnocitrus littoralis* | 2 |
| Perfume concentrate | 0.1 |
| Octyl methoxycinnamate | 3 |

| Anhydrous make-up foundation | |
|---|---|
| Mica | 46.0% |
| Titanium dioxide | 22.4 |
| Talcum | 11.0 |
| Extract D of *Limnocitrus littoralis* | 1.0 |
| Anhydrous silica | 5.0 |
| Nylon-12 | 4.0 |
| Octyl methoxycinnamate | 2.0 |
| Benzophenone-3 | 2.0 |
| Stearic acid | 2.0 |
| Magnesium stearate | 1.5 |
| Colorants and pigments (iron oxides) | 2.5 |
| Perfumes | 0.3 |
| Preservatives | 0.3 |

| Soothing after-sun gel | |
|---|---|
| Glycerol | 5.0% |
| Caprylic/capric/succinic triglycerides | 5.0 |
| Octyl methoxycinnamate | 1.0 |
| Dimethicone copolyols | 0.5 |
| Acrylates/$C_{10}$-$C_{30}$-alkyl acrylate crosspolymer | 0.5 |
| Extract B of *Limnocitrus littoralis* | 3 |
| N-acetylcysteine | 0.2 |
| Preservatives, perfume, colorants | 0.1 |
| Water | qsp |

| Protective sun fluid | |
|---|---|
| Pentacyclomethicone | 49.0% |
| Titanium dioxide | 15.0 |
| Octyl methoxycinnamate | 7.5 |
| Glycerol | 5.0 |
| Phenyl trimethicone | 5.0 |
| Dimethicone copolyols | 3.0 |
| Polymethyl methacrylate | 2.5 |
| Extract C of *Limnocitrus littoralis* | 5 |
| Preservatives, perfume, colorants, neutralizer | 0.1 |
| Water | qsp |

| Anti-wrinkle care cream | |
|---|---|
| Glyceryl stearate + PEG-100 stearate | 6.0% |
| Hydrogenated polyisobutene | 3.0 |
| Squalane | 3.0 |
| Glyceryl caprylate/caprate triglycerides | 3.0 |
| Glycerol | 2.0 |
| Octyl methoxycinnamate | 2.0 |
| Cetostearyl octanoate | 1.5 |
| Beeswax | 1.5 |
| Cetyl alcohol | 1.0 |
| Stearyl alcohol | 1.0 |
| Dimethicone | 1.0 |
| Xanthan gum | 0.2 |
| Extract E of *Limnocitrus littoralis* | 2 |
| Preservatives, perfume, colorants | 0.2 |
| Water | qsp |

What is claimed:

1. A cosmetic composition, comprising:
as an active agent, an alcoholic or aqueous-alcoholic solvent extract of *Limnocitrus littoralis*; and
a cosmetically acceptable vehicle compatible with a topical application, wherein the cosmetic composition is formulated as a cream, gel, lotion, stick, eye shadow or make-up foundation.

2. The composition according to claim 1, wherein said extract is obtained from an aerial part of *Limnocitrus littoralis*.

3. The composition according to claim 2, wherein said extract is obtained from leaves of *Limnocitrus littoralis*.

4. The composition according to claim 1, wherein said solvent is selected from the group consisting of $C_1$ to $C_5$ monoalcohols and $C_2$ to $C_5$ glycols.

5. The composition according to claim 1, wherein said solvent is selected from the group consisting of ethanol, butylene glycol and ethanol/water and butylene glycol/water mixtures.

6. The composition according to claim 5, wherein said solvent is ethanol or an ethanol/water mixture comprising at most 50% of water.

7. The composition according to claim 6, wherein said mixture comprises at most 4% of water.

8. A cosmetic composition, comprising:
   as an active agent, an alcoholic or aqueous-alcoholic solvent extract of *Limnocitrus litoralis*; and
   a cosmetically acceptable vehicle compatible with a topical application,
   wherein said solvent is butylene glycol.

9. The composition according to claim 1, wherein said extract has been subjected to a solid-liquid separation step in order to remove the solid part.

10. The composition according to claim 1, wherein said extract has been subjected to a decolorization step.

11. The composition according to claim 1, wherein said composition comprises from $10^{-4}$% to 5% by weight of dry extract, based on the total weight of the composition, of an extract of *Limnocitrus littoralis*.

12. The composition according to claim 1, wherein said composition also comprises at least one antioxidant.

13. The composition according to claim 1, wherein said composition is in anhydrous form.

14. The composition according to claim 1, wherein said extract is prepared by extracting the *Limnocitrus littoralis* with a solution of butylene glycol.

15. The composition according to claim 14, wherein said solution contains from 0.1 to 1% by weight of said *Limnocitrus littoralis*, based on the weight of butylene glycol.

16. The composition according to claim 1, wherein said active agent is included in an amount sufficient for combating non-pathological skin manifestations of inflammatory origin by means of a soothing effect.

17. The composition according to claim 16, wherein the active agent is included in an amount sufficient for soothing sensations of heat, burning, blotches, pulling, itching or tingling.

18. The composition according to claim 1, wherein said active agent is included in an amount sufficient for stimulating collagen synthesis.

19. The composition according to claim 18, wherein the active agent is included in an amount sufficient for inhibiting, delaying and/or combating the effects of intrinsic and/or photoinduced skin ageing.

20. A method for cosmetic care for soothing non-pathological skin manifestations of inflammatory origin or inhibiting, delaying or combating the effects of intrinsic and/or photoinduced skin aging in a subject which comprises application to parts of a subject's skin in need thereof the composition as defined in claim 1.

21. The method of claim 20, wherein the method provides an anti-wrinkle effect.

22. A method of cosmetic anti-wrinkle care, comprising: applying to parts of a subject's skin in need thereof the cosmetic composition as defined in claim 8.

23. The method of claim 22, wherein the cosmetic composition includes from $10^{-4}$% to 5% by weight of dry extract, based on the total weight of the composition, of an extract of *Limnocitrus littoralis*.

* * * * *